United States Patent [19]

Bruno

[11] Patent Number: 4,869,366
[45] Date of Patent: Sep. 26, 1989

[54] RECEPTACLE ASSEMBLY FOR STORAGE AND DISPOSAL OF POTENTIALLY INJURIOUS IMPLEMENTS SUCH AS USED SCALPEL BLADES, HYPODERMIC NEEDLES AND THE LIKE

[76] Inventor: John Bruno, 77-83 Second Ave., Paterson, N.J. 07514

[21] Appl. No.: 195,384

[22] Filed: May 10, 1988

Related U.S. Application Data

[63] Continuation of Ser. No. 102,810, Sep. 22, 1987, abandoned, which is a continuation of Ser. No. 746,047, Jun. 17, 1985, abandoned.

[51] Int. Cl.$^4$ ............................................. B65D 7/00
[52] U.S. Cl. .................................. 206/370; 206/366; 206/380; 220/410
[58] Field of Search ............... 220/410; 206/370, 366, 206/380, 63.5, 365, 381, 216

[56] References Cited

U.S. PATENT DOCUMENTS

| | | | |
|---|---|---|---|
| 1,713,631 | 5/1929 | Tinsley . | |
| 3,648,875 | 3/1974 | Lundgren | 220/410 |
| 3,746,155 | 7/1973 | Seeley . | |
| 3,836,037 | 9/1974 | Bass | 220/410 |
| 3,946,937 | 3/1976 | Forbes, Jr. et al. . | |
| 4,121,755 | 10/1978 | Meseke et al. | 206/366 |
| 4,188,879 | 2/1980 | Judd | 220/410 |
| 4,315,592 | 2/1982 | Smith | 206/366 |
| 4,351,434 | 9/1982 | Elisha | 206/360 |
| 4,375,849 | 3/1983 | Hanifl . | |
| 4,437,575 | 3/1984 | Hahn | 220/410 |
| 4,452,358 | 6/1984 | Simpson . | |
| 4,466,538 | 8/1984 | Gianni . | |
| 4,485,918 | 12/1984 | Mayer | 206/366 |
| 4,488,643 | 12/1984 | Pepper . | |
| 4,520,924 | 6/1985 | Nelson . | |
| 4,520,926 | 6/1985 | Nelson | 206/366 |
| 4,576,281 | 3/1986 | Kirksey | 206/366 |
| 4,722,472 | 2/1988 | Bruno . | |

OTHER PUBLICATIONS

Advertisement for "Hypo-Hopper" by Porex Medical, copyrighted in 1983.
Brochure for Needle Disposal Devices, Catalog Nos. 8700 and 8720, by Sage Products, Inc., copyright 1981.
Advertisement for "Med-Safe" Disposal Containers Sold by Med-Safe Systems, Inc., copyright 1983.
Brochure for "The Safe Deposit Box" sold by Hemox, Inc., copyright 1981.

Primary Examiner—Joseph Man-Fu Moy

[57] ABSTRACT

A receptacle unit for safely storing potentially infurious implements. The unit comprises a permanent receptacle member being intended to removably receive a disposable member. The permanent receptacle includes a top wall which comprises a first opening to permit insertion of used implement to be discarded.

32 Claims, 4 Drawing Sheets

RECEPTACLE ASSEMBLY FOR STORAGE AND DISPOSAL OF POTENTIALLY INJURIOUS IMPLEMENTS SUCH AS USED SCALPEL BLADES, HYPODERMIC NEEDLES AND THE LIKE

This is a continuation of co-pending application Ser. No. 102,810, filed on Sept. 22, 1987 now abandoned, which in turn is a continuation of then co-pending application Ser. No. 746,047, filed on June 17, 1985, now abandoned.

BACKGROUND AND OBJECTS OF THE INVENTION

The present invention relates generally to receptacles, containers and the like, and, more particularly, to receptacles for safe storage and ultimate disposal of potentially injurious or contaminated implements such as used scalpel blades, hypodermic needles and like devices which pose a risk of causing infection or even disease by exposure to such implements.

With the advent of disposable medical implements such as surgical tools, hypodermic needles, scalpel blades and other sharp implements, a need has developed for a receptacle to safely store such implements after use without risk of exposing people to injury, infection or disease by improper handling, until proper disposal can be made. The tragic outbreak of the highly contagious AIDS disease has dramatically highlighted the need for safer handling, storage and disposal of such implements.

In the case of disposable hypodermic needles, it had been common practice to break or cut the needles prior to discarding the needle and syringe in order to reduce the size of the overall needle/syringe device and to eliminate the sharp point from the needle to reduce the risk of injury which might otherwise result from handling. In breaking or cutting the needles, however, it was determined that a substantial danger existed of accidental puncture during the breaking or cutting operation, thus exposing the holder to possible injury and, further, to possible infection or disease. In addition, any residual medication in the needle was susceptible to splattering onto the person or his clothes and there was a danger that potentially harmful fumes could be inhaled. Furthermore, the blades of the cutting tool became a breeding ground for germs, bacteria and other disease-causing micro-organisms to which the unsuspecting person cutting the needle is unnecessarily exposed.

Recently, an even greater danger has been recognized in connection with the handling and dismantling of used needles and other sharp medical implements. It is now recognized that certain diseases, most notably Hepatitis B, can be transmitted by covert percutaneous —i.e., by merely contacting the contaminated needle or implement.

As a result of the foregoing dangers, the preferred current practice is to dispose of such devices intact. Often, the needles are now re-capped after use with the protective sheaths used during shipment from the manufacturer, in order to prevent injury while carrying the device to a suitable disposal unit. This practice, however, often results in puncture wounds suffered while re-capping the needle point.

Although certain proposals have been advanced for eliminating some of the risks involved in the handling, storage and disposal of hypodermic needles and other sharp medical implements, they generally do not overcome all of the dangers. Often, they become the source of other problems. For example, there are several specially designed containers for storing used hypodermic needles, including some made of all plastic and some made of all cardboard, as identified, for example, in my co-pending application Serial No. 513,616, filed July 14, 1983, the disclosure of which is hereby incorporated by reference herein.

Although such specially designed devices provide adequate results under certain circumstances, they do suffer certain disadvantages. For example, the plastic devices, being made of plastic, can be relatively expensive to use as a disposable storage container. In addition, the plastic and cardboard devices generally have thin or single-layer side walls which do not provide any added margin of safety against possible punctures or poke-through. Furthermore, in all the containers, either the entire syringe/needle or the syringe with the needle stub is dropped vertically into the containers, thus creating a haphazard distribution of needles in the container. Such distribution usually results in an inefficiently filled container and can be the cause of possible injury to the user because of the haphazard arrangements of implements.

Another available device for the storage and disposal of used hypodermic needles is that sold under the designation "MED-SAFE" by Becton Dickenson & Co. of Rutherford, N.J. This device comprises a plastic jug-like container having a detachable circular cover which is cut with a "starburst" pattern to form a plurality of radially inwardly extending flaps. This device suffers similar drawbacks to those described above, including the haphazard distribution of implements dropped into the container. In addition, as used implements are pushed through the "starburst" arrangement of flaps, any medicines or other potentially contaminable liquid on the devices are apt to remain on the upper surfaces of the cover, thereby forming a breeding ground for germs, viruses and infectious diseases. Also, as implements are forced through the "starburst" flaps, contact is invariably made with such residual liquids on the flaps.

As set out in my aforesaid co-pending application, the receptacle disclosed therein (also sold under the mark "D.D.BOX" by D.D.Box Inc. of Paterson, N.J. and Highland Beach, Fla.) overcomes virtually all of the foregoing drawbacks. However, even with the advantages achieved by such receptacle, hospital administrators still express a desire for further safety features in storage/disposal receptacles, generally. For example, hospital personnel express a desire for a storage/disposal container which provides protection against injury from or contact with discarded implements even where the container has been overfilled, and which provides complete protection against poke-through of needles or other implements stored therein. Continuing concern is also expressed for increasing the protection against the risk of disease transmitted by covert percutaneous, and for a means to prevent access to or contact with the implements stored in the container. Also, it is desired that even though the container maybe intended to be disposable, it should nonetheless be decorative so that it will be attractive to look at, especially when placed in patient rooms and other places frequented by patients, visitors and, or course, hospital personnel.

Accordingly, it is an object of the present invention to provide a new and improved receptacle for storage and disposal of hypodermic needles, scalpels and other sharp or pointed implements which pose a health risk by reason of injury, puncture or even mere contact (hereinafter referred to collectively as "potentially injurious implements", or simply "disposable implements"). It is another object of the present invention to provide a new and improved receptacle for storing potentially injurious implements, which is sturdy and resistant to puncture by the implements retained therein, yet permits convenient and complete disposal of the implements.

It is also an object of the invention to provide a new and improved receptacle for storage and disposal of potentially injurious implements, which is adapted to receive implements in a compact side-by-side horizontal configuration for maximum storage capacity. It is another object of the invention to provide such a receptacle which further prevents any implements stored therein from falling out after they have been inserted therein, and which provides a permanently sealable disposable container which can be conveniently discarded in an appropriate disposal facility. In addition, it is an object of the invention to provide such a receptacle which provides protection against contact with or injury from such implements.

It is yet a further object of the present invention to provide a new and improved receptacle for storing potentially injurious implements, which is compact, and can be conveniently mounted to any wall or other desired structure, yet can also be decorated for producing an attractive receptacle which can be installed in doctor offices, patient rooms or other hospital areas.

It is still a further object of the present invention to provide a new and improved receptacle for storage and disposal of potentially injurious implements, which provides complete disposability yet provides a completely secure container that can be locked to prevent access by unauthorized persons. As a result, the receptacle can be safely installed in doctor offices, patient rooms, etc. without fear of entry by unauthorized persons.

The foregoing specific objects and advantages of the invention are illustrative of those which can be achieved by the present invention and are not intended to be exhaustive or limiting of the possible advantages which can be realized. Thus, these and other objects and advantages of the invention will be apparent from the description herein or can be learned from practicing the invention, both as embodied herein or as modified in view of any variations which may be apparent to those skilled in the art. Accordingly, the present invention resides in the novel parts, constructions, arrangements, combinations and improvements herein shown and described.

SUMMARY OF THE INVENTION

Briefly described, the present invention comprises a receptacle assembly for the deposit, storage and ultimate disposal of disposable medical implements, which includes a box-like permanent receptacle member adapted to retain a liner, or disposable receptacle member which conforms generally to the configuration of the permanent receptacle member, for receiving and holding used hypodermic needles, scalpels and like potentially injurious implements, as well as the permanent receptacle member itself. Advantageously, both receptacle members are relatively elongate, and the top portions of both receptacle members are adapted to provide access to their interiors for receiving the implements therein. As preferably embodied, the top portions of said receptacle members are proportioned such that there is provided a limited access receiving chamber into which the implements are first dropped before being fully received in the disposable receptacle member, preferably by an angularly inwardly projecting trap-door closure panel which is generally biased towards an opposite wall member to close the top of the disposable receptacle member but which can be pushed open to allow an implement to drop into the disposable receptacle member for safe storage and ultimate disposal.

Advantageously and as preferably embodied, the top portion of the permanent receptacle member includes one or more openings proportioned to receive the various sizes of implements to be stored therein yet substantially to prevent access to the receiving chamber by a person's hand. The top of the permanent receptacle member also includes a finger access opening (preferably smaller than and different from the implement-drop opening to allow only limited access by a person's hand) to provide limited access by the person's fingers to the closure panel of the disposable receptacle for opening the panel and thereby causing any implement thereon to drop into the disposable receptacle member.

Advantageously, the permanent receptacle member is made of metal (preferably, aluminum for light weight) or other generally impenetrable material, while the disposable receptacle member may be made of corrugated cardboard, stiffened paper or other relatively inexpensive but relatively rigid material adapted to resist puncture by a needle point. In this way, the disposable receptacle member will provide enough puncture resistance to allow it to be safely removed from the permanent receptacle member and carried to an appropriate disposal unit for ultimate disposal. However, the permanent member provides complete assurance against any possible poke-through during use, and, it permits the entire receptacle to be secured (as by locking it) against access by unauthorized persons.

Thus, the permanent receptacle member can be permanently installed at the immediate location(s) where potentially injurious disposal implements are frequently used. When so installed, the receptacle according to the present invention eliminates the need for a person otherwise to carry a used implement (e.g., a used hypodermic needle) to a disposal unit which may be located distant from its place of usage (e.g. a patient's room), with the consequent risk of injury from or contact with the implement while it is being carried to a disposal unit.

It will similarly be appreciated that, because of the nature of the permanent receptacle member, the receptacle assembly according to the present invention can be decorated to complement the furnishings of the room in which the receptacle is installed for an attractive appearance. (This can also help disguise the function of the receptacle from persons who might otherwise be searching for used syringes to put to unlawful use.) The disposable receptacle member would, of course, be imprinted with a suitable legend, including the universal symbol for contaminated sharps, to warn authorized persons of the dangerous nature of the implements stored in the receptacle.

In addition, the permanent receptacle can be locked to prevent unauthorized access to the contents of the receptacle.

It will thus be readily apparent from the foregoing general description, as well as the following detailed description, that the objects and advantages specifically enumerated herein are achieved by the invention as embodied herein. For example, by providing a permanent receptacle member which acts as a protective shell for the disposable receptacle member, a safe and durable receptacle is provided for safely receiving, storing and eventually disposing of potentially injurious implements. In addition, the biased top closure panel of the disposable receptacle provides a "trap door" which, as part of the receiving chamber, minimizes the amount of contact a person must have with the implements when disposing of them.

By providing openings in the top portion of the permanent receptacle member, assurance is provided that a person's hand will not touch a used implement released into the receiving chamber when opening the closure panel of the disposable member, yet safe storage for used implements is provided in the receiving chamber in the event that the disposable receptacle is inadvertently overfilled. However, the disposable receptacle also preferably includes an extra top closure panel which can be sealed over the trough-like recess in the disposable receptacle for safely enclosing any implements which have overfilled the disposable receptacle. It also ensures that any implements which may become dislodged will remain safely sealed within the disposable member.

It will be appreciated by those skilled in the art that the foregoing brief description and the following detailed description are exemplary and explanatory of the invention, but are not intended to be restrictive thereof. Thus, the accompanying drawings, referred to herein and constituting a part hereof, illustrate preferred embodiments of the invention and, together with the detailed description, serve to explain the principles of the invention.

DETAILED DESCRIPTION OF PREFERRED EMBODIMENTS

Figure 1:
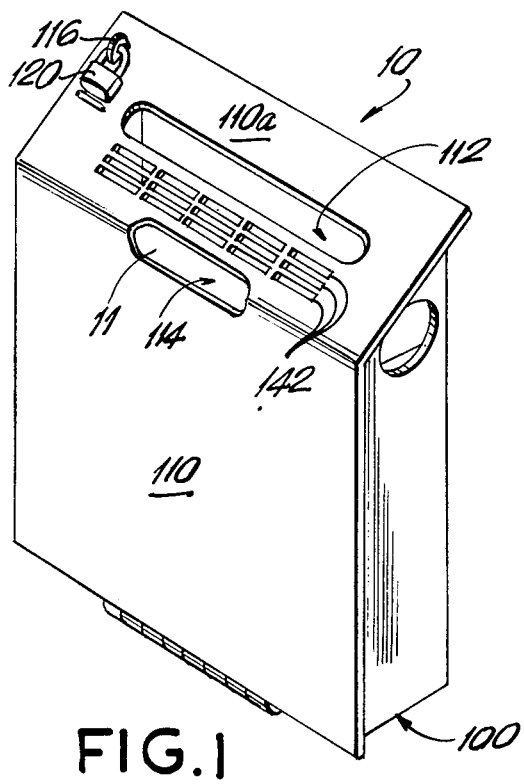
FIG. 1 is a an isometric view of an embodiment of a receptacle assembly according to the present invention.

Turning now to the accompanying drawings wherein like reference characters refer to like parts throughout the various views, there is shown in Figures 1-9, a preferred embodiment of the receptacle assembly (indicated generally at 10) according to the present invention. As here embodied, receptacle assembly 10 comprises a permanent receptacle member which forms an outer housing or shell for a disposable receptacle member which, advantageously, may be a disposable container substantially of the type disclosed in my aforesaid co-pending patent application Ser. No. 513,616, filed July 14, 1983 the disclosure of which is hereby incorporated by reference herein for purposes of this detailed description.

Referring more particularly to FIGS. 1-4, there are shown various illustrations an embodiment of permanent receptacle member for receptacle assembly 10 according to the present invention. As here embodied, receptacle assembly 10 includes a permanent receptacle member (indicated generally at 100) which, advantageously, is adapted to form a housing for, and conform generally to the shape of, the disposable receptacle member (indicated generally at 11) which will be described more fully below. Permanent receptacle 100 includes a back wall 102 which can be adapted to be attached to a wall (preferably by screws inserted through holes 103) or other suitable mounting structure. Projecting outwardly from backwall 102 are sidewalls 104 and 106 and bottom wall 108. Advantageously, a front wall/door (indicated at 110) is hingedly attached at the front of receptacle member 100 (here, along the front edge of bottom wall 108) and is configured so as to substantially close off the front-edges of the side and bottom walls to form a fully enclosed permanent receptacle member.

As here preferably embodied, the upper portion of permanent receptacle 100 is canted to provide, as will be explained in greater detail hereinafter, a receiving chamber within the receptacle assembly. To this end, each of the upper ends of side walls 104 and 106 have upwardly tapering front edges (indicated at 105 and 107, respectively, in FIGS. 2 and 3), and front wall 110 includes an angularly canted upper portion (indicated at 110a) which extends at about the same angular pitch as the angle of taper of front edges 105 and 107. Thus, when front wall 110 is rotated upwardly as indicated by the arrow in FIG. 2, it will fully close the permanent receptacle 100, and it also provides the receiving means for the permanent receptacle member, as will be explained more fully below.

Figure 3:
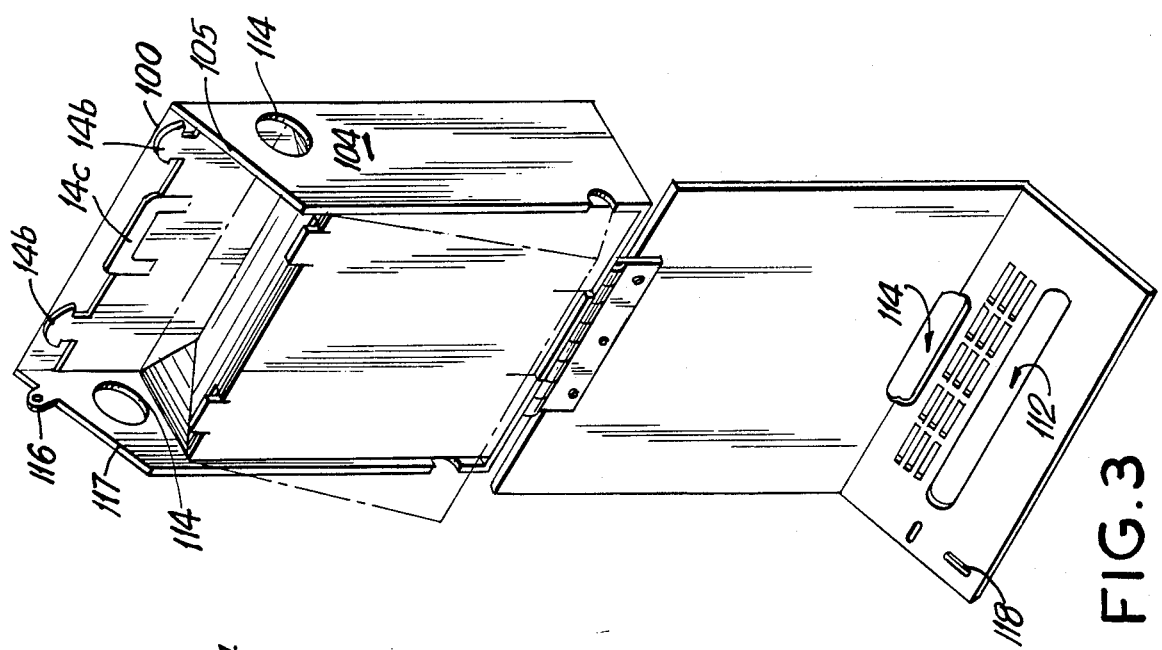
FIG. 3 is a view similar to that of FIG. 2 illustrating installation of an embodiment of a disposable receptacle member as part of the receptacle assembly according to the invention.

Referring specifically to FIG. 3, when front wall 110 of the permanent receptacle member 100 is opened, receptacle 100 is ready to receive a disposable receptacle member 11. (As already indicated, the disposable member preferably has the same general configuration as the permanent receptacle member 110 to permit it to be fully enclosed therein.) With the front wall opened, the disposable member can simply be placed within the permanent receptacle member and retained in place by closing the front wall member.

In order to permit used disposable implements to be inserted into the receptacle assembly, one or more openings are formed at the top of permanent member 100 to allow discarded implements to be dropped into the receptacle assembly. As here preferably embodied, a first elongate opening 112 is formed in canted upper portion 110a. The elongate opening 112 is advantageously limited in size, and is positioned and proportioned so as to permit insertion of a predetermined maximum size of used disposable implement, while substantially preventing a person's fingers from reaching in to touch a used implement which may be lying in the recessed trough of the disposable member (indicated at 15 in FIGS. 5 and 6, as will be explained more fully below). For example, opening 112 may be about 8 inches long and about 1 inch wide to allow entry of most popular size hypodermic needle/syringes up to about 30 cc.

Figure 4:
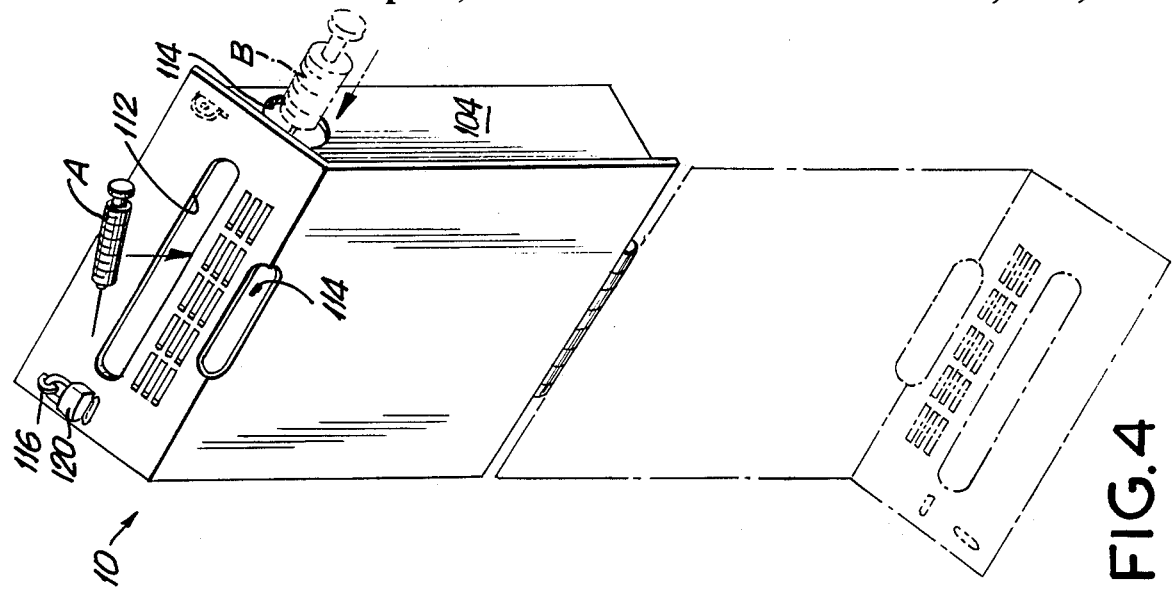
FIG. 4 is a view similar to that of FIGS. 1-3, showing operation of the receptacle assembly according to the present invention.

Moreover, opening 112 is advantageously positioned as high up on canted portion 110a as practical for maximizing the distance between opening 112 and the bottom of trough 15. As illustrated in FIG. 4, the permanent receptacle permits used disposable implements (such as the needle/syringe indicated at A) to be dropped horizontally into the receptacle, for safest handling, through opening 112. At the same time, while needle/syringe A lays at the bottom of trough 15, it remains generally out of reach by a person who might try to touch it by reaching his or her fingers through opening 112.

For larger size needles or implements, a limited diameter opening (indicated at 114) is formed in one (or preferably both) of the side walls 104, 106, in the upper segment bounded by the canted edge segments 105, 107. For example, the opening(s) 114 can be approximately 2" in diameter to accommodate hypodermic needles with oversize syringes (indicated at B in FIG. 4) up to about 50 cc., yet will prevent a person's hands from touching an implement lying within trough 15. (Although all used implements could be inserted into the receptacle through opening 114, use of opening 112 is preferred for depositing the disposable implements because it allows them to be simply and safely dropped in a horizontal orientation.)

Advantageously, permanent receptacle member 100 includes means for securing the receptacle assembly 10 against unauthorized access to the disposable receptacle member 10 contained within permanent receptacle member 100. As here preferably embodied, the securing means comprise an interlocking tongue and slot arrangement, with tongue-like tab 116 projecting upwardly from a canted side wall edge (here, edge 107) to project through a slot 118 formed in upper canted portion 110a of front wall/door 110 when front wall/door 110 is fully closed. Tongue 116 also includes aperture 116a formed therein for receiving the shackle of a lock for completely securing the receptacle assembly. The tongue and slot arrangement could be located on the other side or on both sides as indicated in phantom in FIG. 4.

Figure 2:
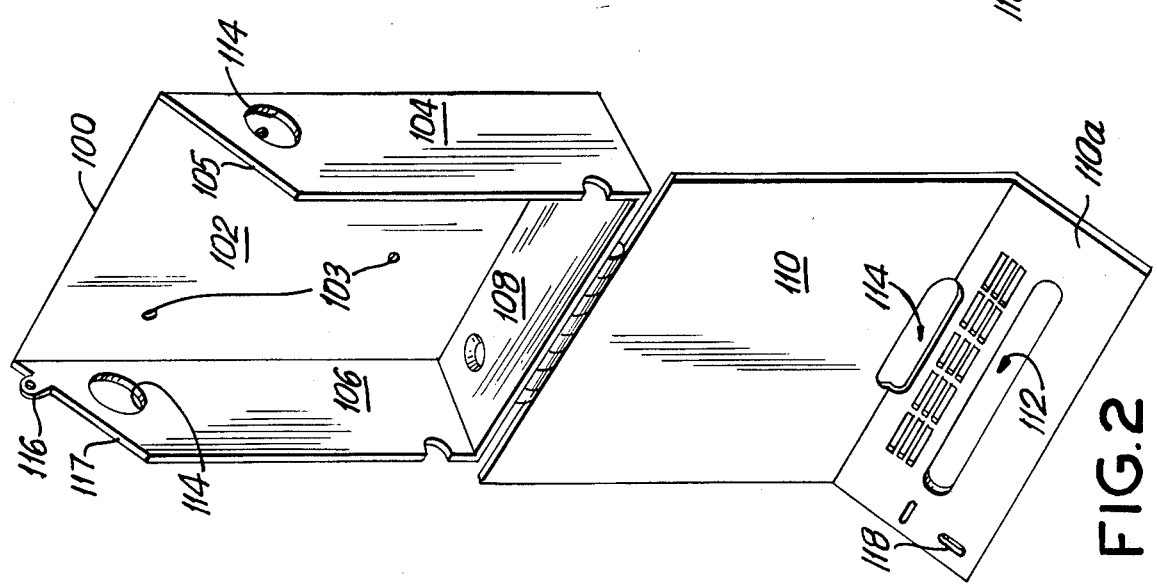
FIG. 2 is a front isometric view of the permanent receptacle member of the embodiment of FIG. 1, in the open configuration.
Figure 8:
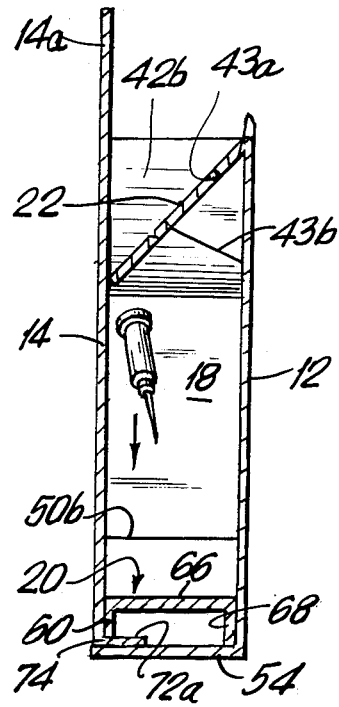
FIG. 8 is a sectional view taken along section lines 8—8 of FIG. 7.
Figure 7:
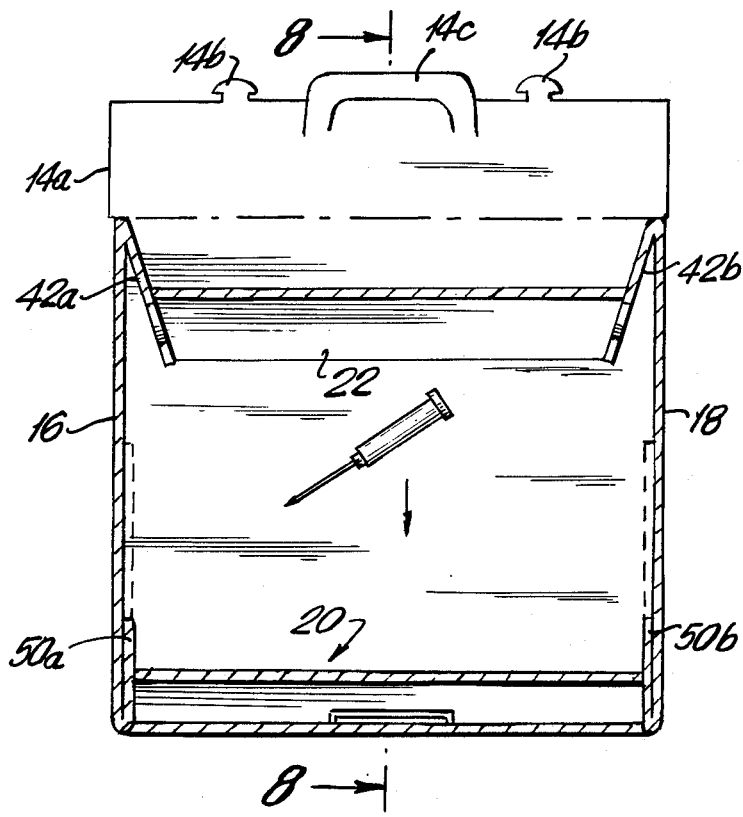
FIG. 7 is a sectional view taken along section lines 7—7 of FIG. 6.

To assemble the receptacle unit according to the present invention, the front wall/door 110 is pulled downwardly to expose the interior of permanent receptacle member 110, as indicated in FIG. 2. A fresh disposable receptacle member 10 (described more fully below) is placed within the interior of the permanent receptacle member, as illustrated in FIG. 3. The front wall/door 110 is then rotated upwardly, as indicated in FIG. 4, until its upper canted portion 110a generally abuts the canted side edges 105, 107, and the tongue 116 projects through slot 118, to close the receptacle unit. Once the receptacle is closed, the shackle of a padlock or like locking device (indicated at 120) is inserted through aperture 116a to secure the receptacle assembly against unauthorized entry.

Advantageously, canted side edges 105, 107 and canted upper portion 110a extend at about 45° with respect to the back wall 102 and the remainder of front-/wall door 110, respectively.

As preferably embodied, the length of slot 118 and the height of tongue 116 are advantageously proportioned such that the slot will "snap" over the top of the tongue in order to permit complete closure of the permanent receptacle member. That is, as the slot initially approaches the tongue, one of its end edges will at least rub against the corresponding edge of the tongue during a portion of the rotational travel of wall/door 110. To accommodate such "snap" action, the outward end of tongue 116 is preferably rounded, as best illustrated in FIGS. 2-3.

It will thus be understood that a force of sufficient magnitude must be exerted in order to force slot 118 over tongue 116. By the same token, a similar but reverse direction force is required to open the front wall-/door. Consequently, even if no securing device is used (such as lock 120), the receptacle assembly will remain reliably closed to keep the disposable receptacle, and the implements stored therein, safely enclosed within the receptacle assembly.

Referring now to FIGS. 5–9, there is shown a preferred embodiment of a disposable receptacle member for the receptacle assembly according to the present invention. As indicated above, the disposable receptacle is, advantageously, essentially the same as the disposable container disclosed in my aforesaid co-pending application, except for certain modifications disclosed herein to facilitate use with permanent receptacle member 100. For convenience, the reference numbers used herein are the same as those used to designate the same or like parts in the disposable receptacle disclosed in my aforesaid co-pending application.

As here preferably embodied, disposable receptacle member 11 includes front wall panel 12, a back wall panel 14 and a pair of oppositely disposed side wall panels, 16 and 18, which maintain the front and back wall panels in spaced apart relation. Bottom wall assembly 20 (advantageously a double-walled member as explained in greater detail in my aforesaid co-pending application) seals off the bottom of disposable receptacle 11 to form a hollow receptacle for discarded implements. The double walled bottom assembly may thus include a pair of bottom panel members (54,66) spaced apart by spacer panels (60,68) and may be secured together by an interlocking tab and slot (72a and 74, respectively). (Tabs 50a and 50b, formed at the ends of the sidewall panels may be folded up into the receptacle at the edges of the bottom assembly). It will be understood however that instead of forming disposable receptacle 11 with a double walled bottom assembly 20, a moisture proof bottom liner made, e.g., of styrofoam, (not shown) could be used to collect any liquids associated with the discarded implements.

As preferably embodied, the top of disposable receptacle 11 is formed with closure means which can be readily opened to permit the deposit of implements to be discarded, yet will otherwise remain closed at all other times to prevent any implements therein from falling out. To this end, flap-like top closure panel 22 is hingedly joined to the top edge of front wall 12 and, preferably, extends angularly inwardly into the receptacle chamber. Advantageously, the width of panel 22 (i.e., the distance from its hinged connection with panel 12 to its inward free end edge, or distal edge) is greater than the corresponding depth of the container (i.e., the distance between the front and back wall panels) to ensure that its inward, or distal, edge resides within receptacle 11 at an angle (preferably of substantial slope) with respect to the top edges of the wall panels. In this way, panel 22 forms a sloped entry trough (indicated at 15) for initially receiving discarded implements and, subsequently, for ensuring that the implements safely drop into the receptacle in a horizontal orientation for storage in side-by-side relation.

Also as indicated in my aforesaid co-pending application, panel 22 provides a barrier for preventing implements from falling out of the container once they are deposited therein. Advantageously, the hinged joinder of panel 22 with the top edge of front panel 12 is self-biased so that the distal edge of panel 22 is constantly urged upwardly to maintain closure of the container. It will thus be understood that the material making up the hinged connection should be generally resilient (or could be reinforced with a piece of tape preferably applied before closure panel 22 is folded into the container) to withstand repeated opening and closing.

Figure 9:
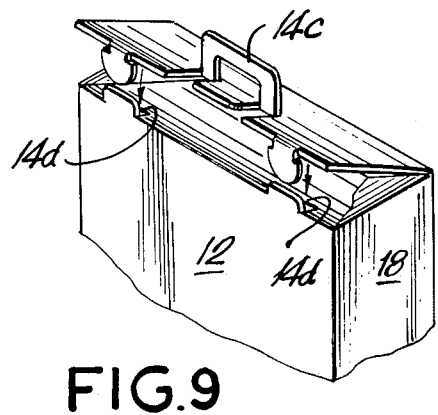
FIG. 9 is a view similar to that of FIG. 6, with partial cut-away, illustrating closure of the disposable receptacle member for final disposal, according to the present invention.
Figure 13:
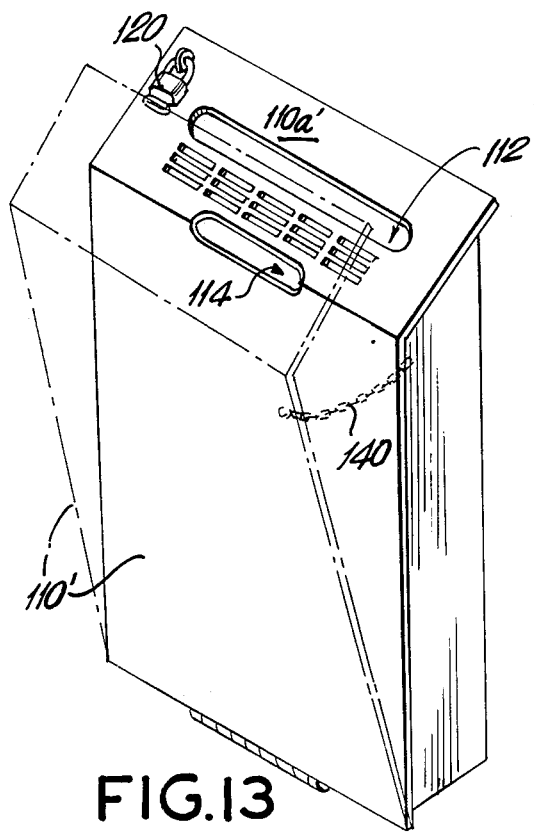
FIG. 13 is a view, similar to that of FIGS. 1-4 of a modified embodiment of a permanent receptacle member according to the present invention.

Also advantageously, back wall panel 14 includes an upstanding panel (indicated at 14a) which projects beyond the top edges of the other container walls. Upstanding panel 14a here provides an additional closure member for sealing the container after it is filled. Panel 14a can simply be folded down onto the top edges of the other wall panels and therefore secured (as by taping panels 14a adjacent panel 12) to fully close the disposable receptacle once it is sufficiently filled with discarded implements. Alternatively, a pair of tabs 14b formed along the upper edge of panel 14a can be inserted into a corresponding pair of slots (each indicated at 14d) formed in the opposite upper edge as indicated in FIG. 9. In addition, a portion of panel 14a can be suitably cut or scored to form handle 14c by which the disposable receptacle member can be safely carried for proper disposal after it has been filled and closed.

Advantageously and as preferably embodied, the disposable receptacle member is made of a single sheet of relatively inexpensive but relatively puncture-resistant material such as corrugated paper or cardboard, stiffened paper or even some plastic materials, as described in detail in my aforesaid co-pending patent application. Where corrugated paper is used, B-flute grade is preferred. Except for expense, corrugated plastic may be preferred when the receptacle assembly is to be used in locations or applications where it will be exposed to water or liquids. It will also be understood that the disposable receptacle member can be made from a single sheet of material as disclosed in my aforesaid co-pending application.

Figure 5:
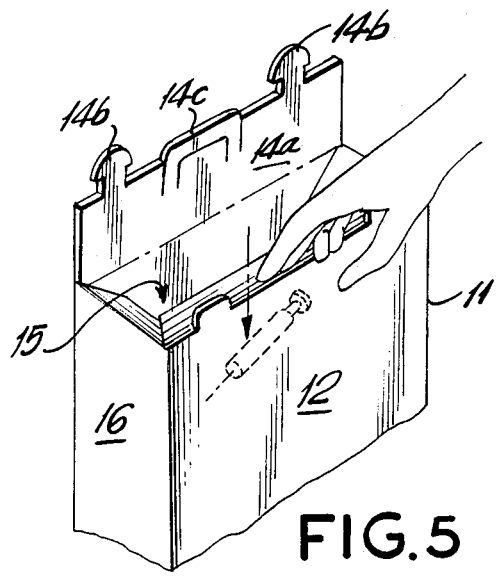
FIG. 5 is an isometric view, with partial cut-away, of a disposable receptacle member (with the permanent receptacle member removed for clarity) illustrating the deposit and storage of implements within the receptacle assembly according to the invention.
Figure 6:
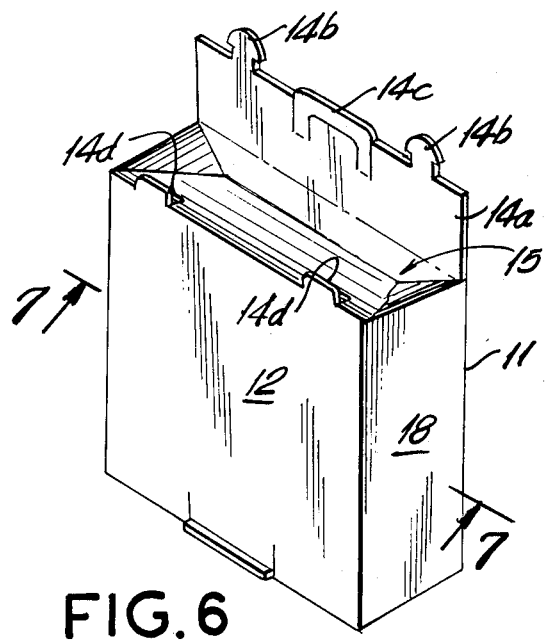
FIG. 6 is an isometric view, similar to FIGS. 1-4, of a preferred embodiment of disposable receptacle member in accordance with to the present invention.

As preferably embodied, and as disclosed in my aforesaid co-pending application, the entry opening of disposable receptacle member 11 is governed by upwardly biased, angularly inwardly extending closure panel 22. Closure panel 22 is pushed inwardly to open the disposable receptacle member and allow a used implement to drop into receptacle 10, as indicated in FIG. 5. Also as disclosed in my co-pending application, each of the side panels, 16 and 18, are formed with identical, but reversed, tab members (indicated at 42a and 42b, respectively, and delineated from the side wall panels by score lines 44) which act as guides for the opening and closing action of closure panel 22. To this end, each tab 42a and 42b is formed with a generally L-shaped cut-out or notch (indicated at 43) which form a stop edge (43a) and a clearance edge (43b) that intersect at an angle of about 75° to about 90° with respect to each other, all as described in greater detail in my aforesaid copending application. It will be understood that stop edges 43a define the upward limit of travel for closure panel 22 and should advantageously be proportioned so that the distal edge of panel 22 is at least closely adjacent, or abutting, panel 14 when panel 22 rests against stop edges 43a.

Also as described in my aforesaid co-pending application, the sides of closure panel 22 are preferably tapered, with a step 22a to provide a narrower inner segment of the closure panel. This narrowing facilitates the interfit between closure panel 22 and the notches formed in the side tabs 42a and 42b and helps reduce friction between closure panel 22 and the side tabs 42a and 42b to ensure proper closure of the disposable receptacle 10.

It will be understood that since tabs 42a and 42b are urged upwardly against the side edges of closure panel 22, they close any gap which otherwise might exist between the side edges of panel 22 and the side wall panels 16 and 18, and thus seal the implements within the container. It will further be understood that tapered side edges of panel 22 facilitate its swinging movement over side tabs 42a and 42b. In addition, indentations 22a serve to recess the innermost edges of panel 22 which actually slide over the tabs, thereby to reduce the friction generated by the movement of panel 22. The juxtaposition of closure panel 22 and side tabs 42a and 42b thus create trough-like recess 15 for receiving used implements for disposal.

Once assembled with a fresh disposable receptacle 11 secured within permanent receptacle 100, the receptacle assembly according to the invention provides a safe and simple means for handling and storage of used implements for subsequent disposal. After use, each disposable implement to be discarded, such as a hypodermic needle, is simply deposited into receptacle 10 by holding it horizontally and dropping it through opening 112 (as illustrated by needle A in FIG. 4). The implement automatically drops into the receiving chamber formed by upwardly canted front wall/door portion 110a and the trough-like recess 15 formed at the top of disposable receptacle 11. The needle automatically falls into the deepest portion of the trough which is preferably adjacent back wall 102 so that the needle rests farthest from both openings, 112 and 114. The person then simply inserts his or her fingers into opening 114 by a sufficient amount to touch panel 22 and push the panel downwardly until the needle simply drops, by its own weight, into the interior of disposable receptacle 11. FIG. 5 illustrates this procedure but with permanent receptacle 100 removed for ease of illustration.

Once the disposable receptacle is filled, the disposable receptacle member can be removed from the receptacle assembly. To remove receptacle 11, the lock 120, if used, is unlocked and removed by an authorized person, and the front panel/door 110 is urged open. (As indicated above, sufficient force must be exerted to force slot 118 over locking tongue 116.) Front panel/door 110 is then fully opened to expose the filled disposable receptacle member. The additional top panel 14a preferably should be folded down and secured (as by inserting tabs 14b into slots 14d and, if possible, taping it closed as well to provide a secure additional closure means). The disposable insert can then be safely lifted out of the permanent receptacle by the handle member 14c and carried to the ultimate disposal unit or station.

In order to ensure that a person's hand can extend only a limited amount into the receiving chamber, second opening 114 can be about 4 inches long and about one inch high. In addition, opening 114 is advantageously located at the point of joinder of front wall/door 110 and its canted portion 110a, which is also adjacent the top edge of disposable receptacle 11. In this way, closure panel 22 will be immediately accessible to a person's hand so there will be no reason to try to reach deeper into the receptacle chamber.

Figure 10:
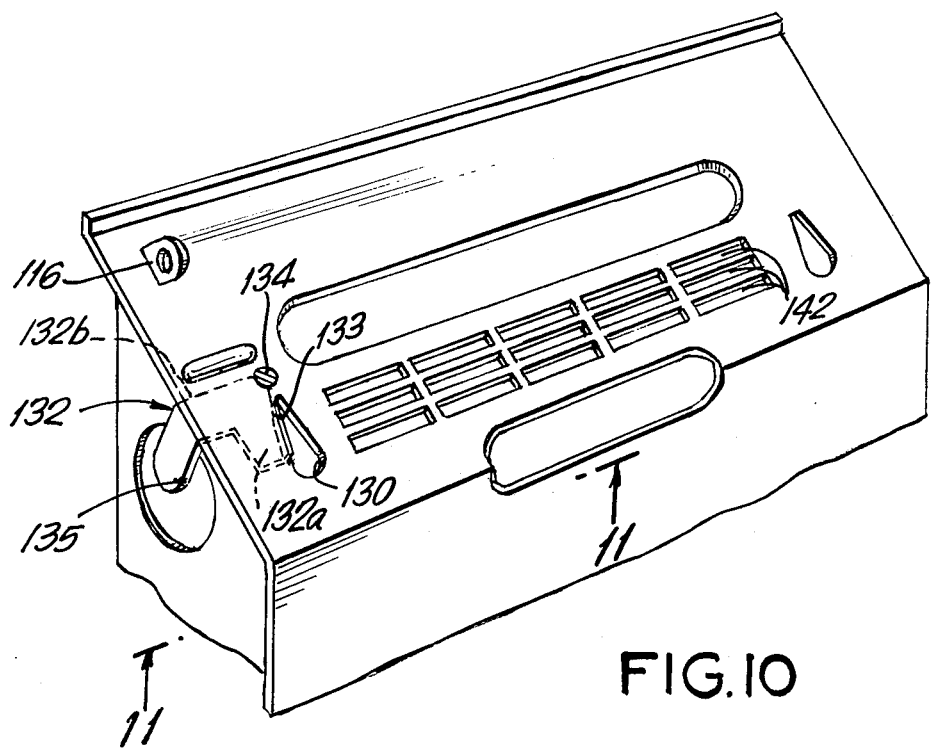
FIG. 10 is a view of the top of a modified version of permanent receptacle member showing another aspect of the present invention.
Figure 11:
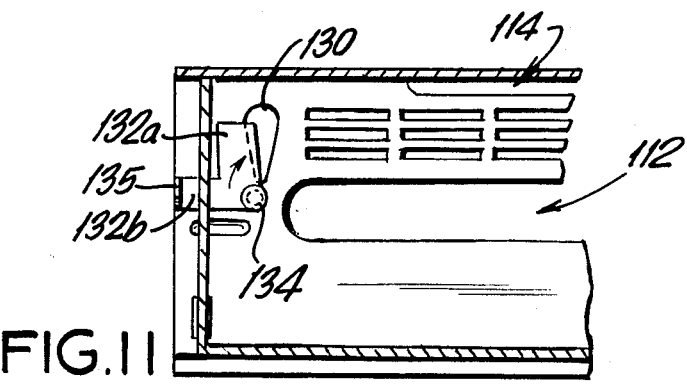
FIG. 11 is a partial sectional view taken along lines 11—11 of FIG. 10 (looking up from within), further illustrating the structure of the feature shown in FIG. 10.
Figure 12:
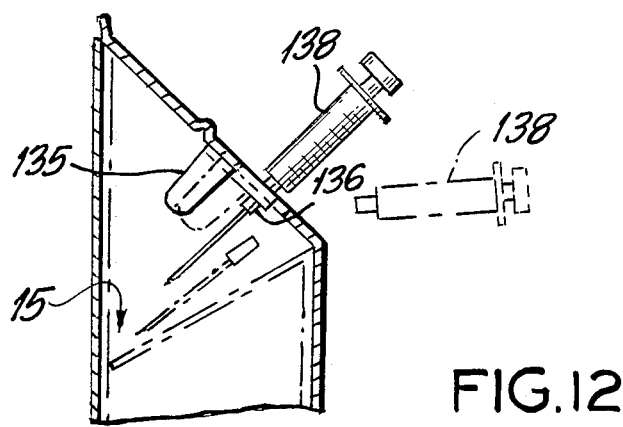
FIG. 12 is a side view, partially in section, of the embodiment of FIGS. 10 and 11 illustrating operation of the structure shown in FIGS. 10 and 11.

Turning now to FIGS. 10–12, there is shown another aspect of the present invention, by which the receptacle assembly can be adapted to safely dismantle and store large needles for which removal of the needle is required or desired. An example of such a needle device is the blood taking device sold under the designation "VACUTAINER" by Becton Dickenson, which includes a relatively elongate needle coupled to a vile or syringe. Because the vile portion is repeatedly used, it is important to remove the needle after use to eliminate any danger of puncture by or contact with the needle.

In order to provide for the removal of the needle portion from any such device, the canted upper portion 110a of front wall/door is formed with an additional opening (here, generally tear-drop shaped opening 130) into which the needle can be inserted. Grasping means are associated with opening 130 to grasp the needle so that it can be removed from the syringe or vile portion (as by rotating the syringe until the needle drops off).

As here embodied, an L-shaped arm member 132 is pivotally attached (by, e.g., a screw or rivet 134) to the underside of canted upper portion 110a. One leg (indicated at 132a) of the L-shaped member is adapted to bear against the needle, while the other leg 132b can conveniently be used for moving the bearing leg 132a into and out of engagement with the needle. To facilitate the grasping function, leg 132a includes a flange portion (indicated at 133) which is bent out of the plane of leg 132a to project into opening 130. Flange 133 serves not only to provide a bearing surface area for grasping the needle hub but it also limits the rotational movement of the L-shaped member. Leg 132b similarly includes a downwardly projecting tab 135 to facilitate moving the L-shaped member into and out of abutting engagement with the needle to be removed.

In operation, then, the needle to be removed is inserted into tear-drop opening 130. The bearing leg 132a is then rotated to graspingly engage the needle by rotating member 132 in the direction of the arrow in FIGS. 10 and 11. With the leg 132a urged against the needle hub indicated at 136 in FIG. 12, the syringe (138) is twisted until it is released from the needle. Thereafter, the leg 132a can be released and the needle will drop into the trough at the top of disposable insert 11. The syringe can then be dropped through opening 112 (or opening 114 if it is oversized), and panel 22 pushed down, as described above, to safely store the device for subsequent disposal. In this way, a person does not have to touch the needle at all during either the needle removal or the needle disposal operations.

As indicated above, the permanent and disposable receptacles are generally the same size, except that the permanent receptacle will generally be taller by about the vertical distance of upper canted panel 110a. Thus, as disclosed in my aforesaid co-pending patent application, the inner disposable receptacle can be as large as about 20 inches tall, 10 inches wide and 3 inches deep. In those instances, the degree of opening of the front wall/door (indicated at 110') may, advantageously, be limited by chain 140. In this way, the elongated front/wall door 110 need not be rotated a full 180° (and thereby protrude into the room which may be awkward or inconvenient) in order to replace the disposable receptacle. Of course, such chain can be used with any size receptacle assembly.

Also advantageously, the canted panel 110a may also include slots or vents (indicated at 142) to facilitate visual inspection of the trough at the top of the disposable receptacle 11. As preferably embodied, each slot 142 is very small as to allow only visual access to the interior of the permanent receptacle while preventing access by a person's figures. For example, the slots can be about 1 ⅜ inches long and about ¼ inch wide.

It will be appreciated by those skilled in the art that the present invention in its broader aspects is not limited to the particular embodiments shown and described herein, and that variations may be made which are within the scope of the accompanying claims without departing from the principle of the invention and without sacrificing its chief advantages.

What is claimed is:

1. A receptacle assembly for safely storing potentially injurious implements such as hypodermic needles, scalpel blades and the like, comprising:

a permanent receptacle member generally in the configuration of a fully enclosable generally box-like enclosure, having a wall structure comprising a back wall portion disposed between a pair of oppositely disposed side wall portions, a front wall portion opposite said back wall portion, a bottom wall portion along bottom edges of said front, back and side wall portions and an inclined top wall portion disposed generally opposite said bottom wall portion but extending at an acute angle generally between said front and back wall portions along their upper edges, said top wall portion including a first opening proportioned to permit insertion of used implements to be discarded, one of said wall portions being attached so as to permit opening and closure of said permanent receptacle member when desired; and a disposable receptacle member proportioned to fit within said permanent receptacle member when said permanent receptacle member is opened and to be substantially fully enclosed within said permanent receptacle member when closed, said disposable receptacle member being adapted to receive used implements through its top after used implements are inserted through said first opening, and said inclined top wall portion providing a receiving chamber above said disposable receptacle member and spacing said opening from said receiving means of said disposable receptacle member, such that used implements can be deposited and stored in said receptacle assembly for disposal by simply dropping them through said first opening in said permanent receptacle member for collection in said disposable receptacle member which, when filled with used implements, can be safely removed from the permanent receptacle member and sealed for ultimate disposal while the permanent receptacle member can be refitted with a new disposable receptacle member for storing another quantity of used implements, said spacing of said opening from the top of the disposable receptacle member acting to prevent hand access to potentially contaminated surfaces or implements within said receptacle assembly.

2. A receptacle assembly according to claim 1, wherein said first opening of said permanent receptacle member is generally slot-like and proportioned substantially resist hand-entry therethrough.

3. A receptacle assembly according to claim 2, wherein said disposable receptacle member includes an angularly inwardly inclined closure panel member at its top, said closure panel member being adapted to be pushed inwardly of said disposable member to permit a used implement to drop into said disposable receptacle member yet, being urged toward an opposite wall of said disposable member, to substantially close said disposable receptacle for preventing access to the contents of said disposable receptacle member.

4. A receptacle assembly according to claim 3, wherein said closure panel member normally extends angularly inwardly of said disposable receptacle member to form a trough-like recess at the top of said disposable receptacle member for initially receiving used implements to be stored therein and, after said closure panel is pushed inwardly, to permit the implements to drop into said disposable receptacle assembly without requiring any handling by a person.

5. A receptacle assembly according to claim 4 wherein said wall structure includes a second opening located at a point generally near said closure panel member of said disposable receptacle member, said second opening proportioned to permit limited access by a person's fingers to the closure panel member of said disposable receptacle member for operating the closure panel.

6. A receptacle assembly according to claim 4, wherein said front and inclined top wall portions are integrally formed to form a front wall/door member hingedly attached to another of said wall portions to permit removal and installation of disposable receptacle members out of and into said permanent receptacle member, said side wall portions having upwardly tapered edges at their upper ends extending to said back wall portion angularly at generally the same slope as said inclined top wall portion of said front wall/door member when said permanent receptacle member is closed.

7. A receptacle assembly according to claim 6, wherein said front wall/door member further includes a hand access opening which is proportioned to permit a person's hand to reach into said permanent receptacle member to operate said closure panel of said disposable receptacle member yet substantially prevent the person's hand from touching an implement lying in said trough-like recess.

8. A receptacle assembly according to claim 7, wherein first said slot-like opening is formed generally at an upper portion of said inclined top wall portion generally to maximize the distance between said slot-like opening and said trough-like recess to prevent access to an implement in said trough-like recess by a person reaching into said slot-like opening, and wherein said hand-access opening is located generally along a line of joinder of said inclined top wall portion and said front wall portion and generally coinciding with a top edge of said disposable receptacle member adjacent the closure panel of the disposable receptacle member.

9. A receptacle assembly according to claim 8, wherein at least one of said side wall members includes a third opening in a portion bounded by its said upwardly tapering edge, said third opening being proportioned to receive relatively oversized implements such as hypodermic needles up to 50 cc. in size.

10. A receptacle assembly according to claim 7, which further includes means for securing said front wall/door member to prevent access by unauthorized persons to the disposable receptacle member within said permanent receptacle member.

11. A receptacle assembly according to claim 10, wherein said securing means comprise a tongue-like member on one of said side wall members and a corresponding slot on said front wall/door, proportioned and positioned to receive said tongue-like member when said front wall/door is closed, said tongue-like member having an aperture therein to receive a securing device such as a lock shackle.

12. A receptacle assembly according to claim 11, wherein said tongue-like member projects outwardly from at least one of said upwardly tapering side wall edges, and wherein said slot is formed in the canted panel portion of said front wall/door member.

13. A receptacle assembly according to claim 12, wherein said slot and said tongue-like member are proportioned and positioned relative to each other to contact each other at least upon initial engagement such that when a sufficient force is exerted, the tongue-like member is surmounted by said slot in a snapping-like action to keep said front wall/door closed.

14. A receptacle assembly according to claim 7, wherein said inclined top wall portion of said front wall/door member includes a second aperture, and which further includes grasping means associated with said second aperture and operable for holding an object inserted into said second aperture, such as a needle of a hypodermic needle/syringe device, such that the needle can be removed from the syringe and it will drop automatically into the trough-like recess of the disposable receptacle member.

15. A receptacle assembly according to claim 14, wherein said grasping means includes a generally L-shaped member pivotally mounted to said inclined top wall portion adjacent said second opening, said L-shaped member having a first leg adapted to cooperate with an edge of said second opening to grasp an object inserted thereinto, and a second leg for moving said first leg towards and away from said second opening edge.

16. A receptacle assembly according to claim 15, wherein said second aperture has a generally tear-drop shape, and wherein said first leg includes an up-turned segment projecting into said tear-drop shaped second aperture to provide a bearing surface of relatively substantial area for grasping an object inserted into the second aperture.

17. A receptacle assembly according to claim 4, wherein said disposable receptacle member further includes an additional closure panel member adapted to be closed over the top of said disposable receptacle for closing and sealing the disposable receptacle after it is filled with discarded implements.

18. A receptacle assembly according to claim 17, wherein said disposable receptacle member includes a handle associated with said additional closure panel for permitting said disposable receptacle member to be safely carried to its ultimate disposal destination.

19. A receptacle unit for safely storing potentially injurious implements such as hypodermic needles, scalpel blades and the like until ultimate disposal can be made, comprising:

a permanent receptacle member being adapted to removably receive and essentially fully contain a disposable receptacle member in which used implements are stored and subsequently transported for ultimate disposal along with the disposable receptacle member, said permanent receptacle member being generally in the configuration of a fully enclosable generally box-like enclosure and having a wall structure comprising a back wall portion disposed between a pair of oppositely disposed side wall portions, a front wall portion opposite said back wall portion with said back wall portion extending higher than said front wall portion, a bottom wall portion along bottom edges of said front, back and side wall portions and an inclined top wall panel portion disposed generally opposite said bottom wall portion, but extending at an acute angle generally between said front and back wall portions along their upper edges, said top wall portion including a first opening proportioned to permit insertion of used implements to be discarded, one of said wall portions being attached so as to permit opening and closure of said permanent receptacle member when replacement of the disposable receptacle member is desired, such that used implements can be safely stored within said receptacle unit by simply dropping them through the first opening in said permanent receptacle member for collection in said disposable receptacle member which, when filled with used implements, can be removed from the permanent receptacle member and sealed for ultimate disposal while the permanent receptacle member can be refitted with a new disposable receptacle member for storing another quantity of used implements said inclined top wall portion providing ready inspection of the fill condition of implements within the disposable receptacle member.

20. A receptacle unit according to claim 19, wherein said first opening in said permanent receptacle member is generally slot-like and proportioned to substantially resist hand-entry therethrough.

21. A receptacle unit according to claim 20, wherein said permanent receptacle member further includes a second slot-like opening to permit limited access by a person's hand to a movable closure panel formed on the disposable receptacle member retained therein.

22. A receptacle unit according to claim 21, wherein said front and inclined top wall portions are integrally formed to form a front wall/door member hingedly attached to another of said wall portions to permit removal and installation of a disposable receptacle member out of and into said permanent receptacle member, said side wall portions having upwardly tapered edges at their upper ends extending to said back wall portion angularly upwardly at generally the same slope as said inclined top wall portion of said front wall/door member when said permanent receptacle member is closed.

23. A receptacle unit according to claim 22, wherein said front wall/door panel further includes a hand access opening which is proportioned to permit a person's hand to reach into said permanent receptacle member to operate a closure panel of a disposable receptacle member retained therein, yet substantially prevent the person's hand from touching any implement therein.

24. A receptacle unit according to claim 23, wherein said first slot-like opening is formed generally at an upper portion of said inclined top wall portion generally to maximize the distance between said first slot-like opening and a disposable receptacle member retained therein to prevent access to an implement in a disposable member by a person attempting to reach into said slot-like opening, and wherein said hand-access opening is located generally along a line of joinder of said inclined top wall portion and said front wall portion.

25. A receptacle unit according to claim 24, wherein at least one of said side wall members includes a third opening in a portion bounded by its said upwardly tapering edge, said third opening being proportioned to receive relatively oversized implements such as hypodermic needles up to 50 cc. in size.

26. A receptacle unit according to claim 23, which further includes means for securing said front wall/door member to prevent access by unauthorized persons to a disposable receptacle member within said permanent receptacle member.

27. A receptacle unit according to claim 26, wherein said securing means comprise a tongue-like member on one of said side wall members and a corresponding slot on said front wall/door, proportioned and positioned to receive said tongue-like member when said front wall/door is closed, said tongue-like member having an aperture therein to receive a lock shackle.

28. A receptacle unit according to claim 27, wherein said tongue-like member projects outwardly from at least one of said upwardly tapering side wall edges, and wherein said slot is formed in the inclined top wall portion of said front wall/door member.

29. A receptacle unit according to claim 28, wherein said slot and said tongue-like member are proportioned and positioned relative to each other to contact each other at least upon initial engagement such that when a sufficient force is exerted, the tongue-like member is surmounted by said slot in a snapping-like action to keep said front wall/door closed.

30. A receptacle unit according to claim 23, wherein said inclined top wall portion of said front wall/door member includes a second aperture, and which further includes grasping means associated with said second aperture and operable for holding an object inserted into said second aperture, such as a needle of a hypodermic needle/syringe device such that the needle can be removed from the syringe and it will drop automatically into a disposable receptacle member retained within said permanent receptacle member.

31. A receptacle unit according to claim 30, wherein said grasping means includes a generally L-shaped member pivotally mounted to said inclined top wall portion adjacent said second opening, said L-shaped member having a first leg adapted to cooperate with an edge of said second opening to grasp an object inserted thereinto, and a second leg for moving said first leg towards and away from said second opening edge.

32. A receptacle unit according to claim 31, wherein said second aperture has a generally tear-drop shape, and wherein said first leg includes an up-turned segment projecting into said tear-drop shaped second aperture to provide a bearing surface of relatively substantial area for grasping an object inserted into the second aperture.

* * * * *